(12) United States Patent
Rosenblatt et al.

(10) Patent No.: US 7,806,894 B1
(45) Date of Patent: Oct. 5, 2010

(54) HEMOSTASIS AND TRANSECTION OF TISSUE

(75) Inventors: Peter L. Rosenblatt, West Newton, MA (US); Anthony J. DiSciullo, Westwood, MA (US)

(73) Assignee: New England Association of Gynecologic Laparoscopists, LLP, Westwood, MA (US)

( * ) Notice: Subject to any disclaimer, the term of this patent is extended or adjusted under 35 U.S.C. 154(b) by 768 days.

(21) Appl. No.: 11/770,714

(22) Filed: Jun. 28, 2007

Related U.S. Application Data

(60) Provisional application No. 60/806,031, filed on Jun. 28, 2006.

(51) Int. Cl.
*A61B 18/12* (2006.01)
(52) U.S. Cl. .............................. 606/47; 606/49; 606/50
(58) Field of Classification Search ................... 606/41, 606/45–50, 113
See application file for complete search history.

(56) References Cited

U.S. PATENT DOCUMENTS

| | | | |
|---|---|---|---|
| 5,318,564 A * | 6/1994 | Eggers | 606/47 |
| 5,611,803 A * | 3/1997 | Heaven et al. | 606/114 |
| 5,746,747 A | 5/1998 | McKeating | |
| 6,616,659 B1 | 9/2003 | de la Torre et al. | |
| 6,852,108 B2 | 2/2005 | Barry et al. | |
| 7,087,053 B2 * | 8/2006 | Vanney | 606/41 |
| 2007/0027450 A1 * | 2/2007 | Nezhat et al. | 606/45 |

* cited by examiner

*Primary Examiner*—Michael Peffley
(74) *Attorney, Agent, or Firm*—Scott E. Kamholz; Foley Hoag LLP

(57) ABSTRACT

A laparoscopic cautery instrument may include an elongate shaft, a handle coupled to the shaft and moveable with respect to the shaft, an insulation ring, and a monopolar cautery wire. A laparoscopic cautery instrument may include an elongate shaft, a handle coupled to the shaft and moveable with respect to the shaft, a monopolar cautery wire, and an electrical conductor.

20 Claims, 17 Drawing Sheets

HEMOSTASIS AND TRANSECTION OF TISSUE

CROSS-REFERENCE TO RELATED APPLICATIONS

This application claims the benefit of U.S. provisional application Ser. No. 60/806,031, filed Jun. 28, 2006, which is hereby incorporated herein by reference. The subject matter disclosed herein was also disclosed in U.S. provisional application Ser. No. 60/694,163, filed Jun. 27, 2005, which is hereby incorporated herein by reference as evidence of constructive reduction to practice.

FIELD

The disclosed systems and methods relate generally to systems and methods for achieving hemostasis and transection of tissues during surgery. More specifically, the disclosed systems and methods relate to surgical instruments and that deliver electrical current to tissues.

BACKGROUND

Surgery may involve control of vascular structures that supply blood to tissues, in order to prepare the tissue for removal from the body. For example, hysterectomy, whether performed abdominally, vaginally, or laparoscopically, requires control of the blood supply to the uterus, namely the uterine and ovarian arteries, before the organ can be transected and removed. With laparoscopic supracervical hysterectomy (LSH), for example, the technique often involves ligation of the uterine-ovarian (or infundibulo-pelvic) ligaments, the broad and cardinal ligaments, the last of which contains the uterine arteries. Several techniques are used to transect these tissues and ligate the blood vessels contained within them including mono- and bi-polar electrocoagulation, staples, sutures and the harmonic scalpel. Once the uterine arteries have been ligated, the cervix may be amputated by one of several methods, including monopolar or bipolar cautery, the harmonic scalpel, or by cutting the cervix with scissors. These techniques, while effective, usually take significant time and skill, especially in avoiding injury to neighboring structures, including the bowel and ureters. Visualization of this area is essential during the amputation of the cervix, and is often hampered by an enlarged uterus, the presence of lower uterine segment or cervical fibroids, or by bowel that is difficult to retract from the cul-de-sac.

SUMMARY

The present disclosure provides systems and methods for surgical hemostasis and transection of tissues. In one exemplary embodiment, a laparoscopic instrument includes a cylindrical shaft, which is placed into the abdomen or pelvis, through a trocar port. Once placing the instrument inside the body, the surgeon deploys it by pushing a syringe-like mechanism or other actuator outside the body. This introduces a double-ring that opens up within the peritoneal cavity. The outer ring, referred to as the stabilization ring, may be wide and thin, like a ribbon, and may be electrically insulated. Within or attached to the outer ring may be a metallic, plastic, or otherwise stiff material that maintains the circular shape of the ring once it has been deployed inside the body. The inner ring, referred to as the transection wire, is adherent to the outer ring during deployment, but may be withdrawn into the cylindrical shaft independently of the outer ring, and an electrical current is applied to the wire.

After the uterine arteries have been ligated during the supracervical hysterectomy by one of several means, as described above, the device may be introduced through one of the laparoscopic trocar ports into the peritoneal cavity. The rings are then deployed by pressing the mechanism on the handle, which opens the ring, and these rings are placed over the uterine fundus like a lasso. The axis of the inner and outer rings may be deviated in relationship to the axis of the hollow cylinder, in order to position the rings in the proper position. This change in the axis of the rings may be performed with an articulating mechanism, or the ring may be simply bent by pushing up against tissue in the body. The device is brought down approximately to the level of the internal cervical os, and the rings are cinched down around the cervix by pulling back on the syringe-like mechanism. Once the seal is tight around the cervix, the outer ring may be locked into place, so that it does not loosen up. Any uterine manipulator, which may be metallic or plastic, should be removed from the cervix at this point. The instrument is attached to an electrical generator and a monopolar current is applied to the inner ring. At the same time, the inner transection wire is withdrawn through the tissue and into the cylindrical shaft. The outer stabilization ring holds the cervix in place and also acts to protect surrounding tissues from injury, since it may be insulated. Once the wire has been completely withdrawn into the shaft, a visual, tactile or auditory signal may be used to indicate to the surgeon that the transection is complete, and the electrical current is stopped. Alternatively, once the wire has been withdrawn back into the cylinder, the electric current may automatically shut off. This action separates the uterine fundus from the cervix. The stabilization ring may then be loosened, and withdrawn back into the cylindrical shaft of the instrument. At this point, the instrument may be removed from the body. The uterine itself would next be removed from the body, with one of several methods, including morcellation or posterior colpotomy.

In another embodiment, the inner transection wire may be insulated except for the outer half or other proportion of the distal segment of the loop.

In another embodiment, the outer stabilization ring may have a second wire embedded within it, which may be exposed on the inside of the ring. This outer ring wire may be exposed circumferentially, or it may only be exposed on either side for several centimeters, which would correspond with the location of the uterine arteries. This technique may be used when the surgeon is able to transect lateral tissues, such as the broad ligament, but does not or can not ligate the uterine vessels. The rings are deployed as stated above and cinched down around the cervix. Bipolar electrical current is then applied, which causes cauterization of the uterine arteries. The surgeon may look for several cues that the cauterization is complete, such as an auditory signal from an ammeter (indicating that the tissue has completed coagulation), or visual confirmation that the uterus has become cyanotic from cauterization of its blood supply. Once the surgeon has determined that the blood supply has been ligated, the bipolar energy is turned off and monopolar energy is applied to the inner transection wire, as described above. The outside of the outer stabilization ring may have visual markings that indicate the location of the outer ring conductive elements.

In another embodiment, the outer insulated stabilization wire may have a channel running within and holes on the outside, inside or along the edges of the outer ring. This channel may be connected to a channel that runs throughout the length of the cylinder and is attached to a suction canister.

Once cauterization begins (either for the uterine arteries or to transect the uterus), suction is activated (either manually or automatically, when electrocoagulation is engaged), which may control the amount of smoke that is generated from the device. The channel ring may also be coupled to a fluid source under positive pressure and thereby provide irrigation to the surgical site.

In another embodiment, the inner and outer wires may come out from the end of the instrument without a ring configuration. The surgeon would manually grasp the ends of the wires, which may have an attachment device located on the end of the wires, and bring the wires around the cervix. The surgeon would then attach the distal end of the wires to another position along the wire; thus, creating a loop configuration. This may be useful, for example, in cases where the uterus is too large to place the loop over the top of the uterine fundus.

BRIEF DESCRIPTION OF THE DRAWINGS

These and other features and advantages of the systems and methods disclosed herein will be more fully understood by reference to the following detailed description in conjunction with the attached drawings in which like reference numerals refer to like elements through the different views. The drawings illustrate principles of the systems and methods disclosed herein and are not necessarily to scale. Implied absolute or relative dimensions are not limiting but are instead provided for illustrative purposes.

DETAILED DESCRIPTION

For clarity and convenience, a number of exemplary embodiments will be described relating to a particular anatomic site, the female pelvis. However, it will be readily apparent to one of ordinary skill in the art that the disclosed systems and methods may be employed in a wide variety of anatomical settings to treat a broad range of abnormalities.

Figure 1:
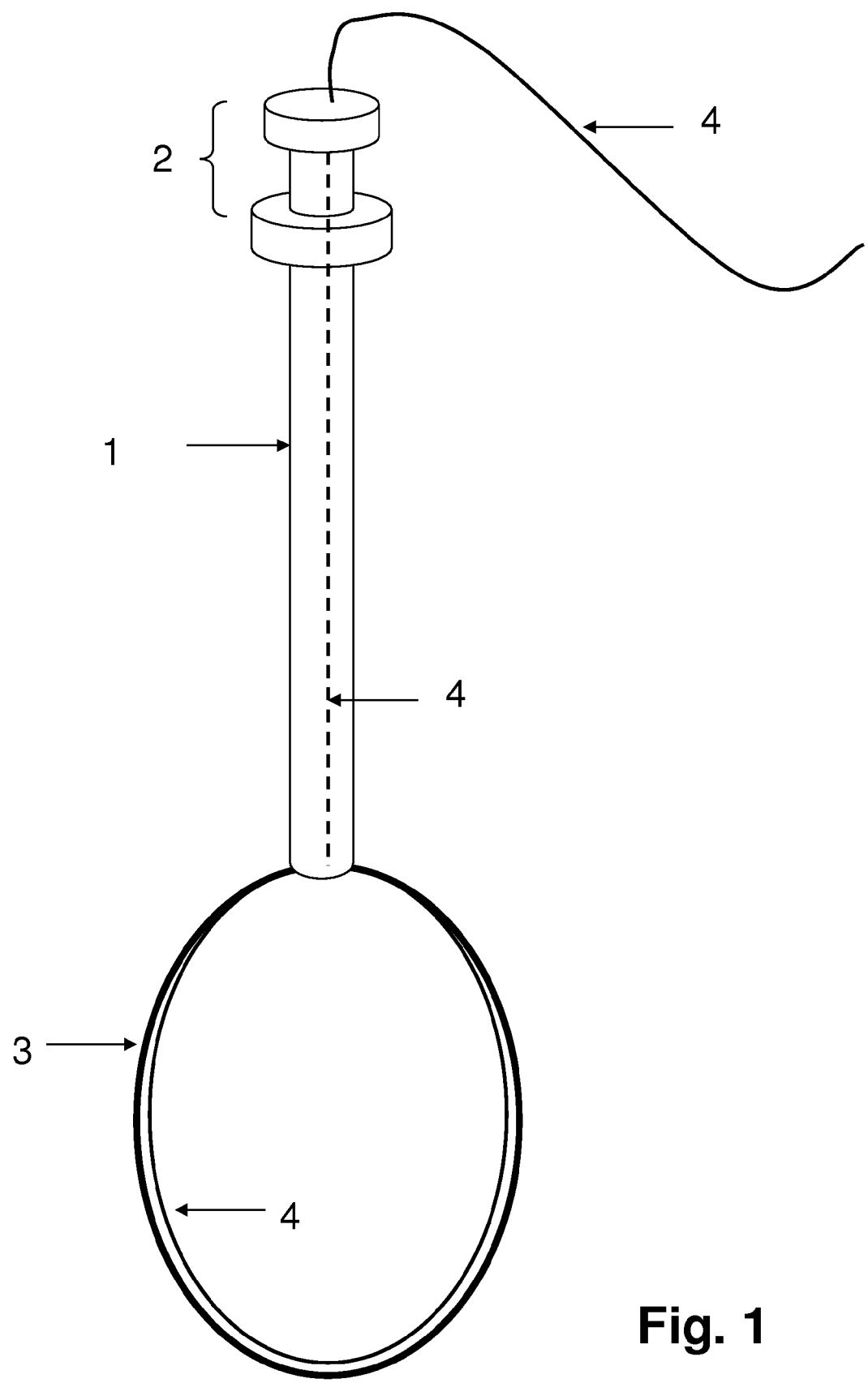
FIG. 1 depicts and exemplary embodiment of a double-ring device, with a cylindrical shaft, a syringe like hand-activated handle that deploys and retracts the double ring system, and a device that retracts the transection wire.

FIG. 1 illustrates the general design of the instrument. It may include a cylindrical hollow tube (1), a handle (2) and two rings that are deployed out from the end of the cylindrical tube: an outer insulated stabilization ring (3) which is thin but wide (as a ribbon), and an inner transection wire (4), which connects to a wire that runs up the cylinder, out through the handle and connects to an electrical generator. Pushing in on the handle deploys the two rings together out from the end of the cylinder and pulling back on the handle draws the rings back into the cylinder.

Figure 2:
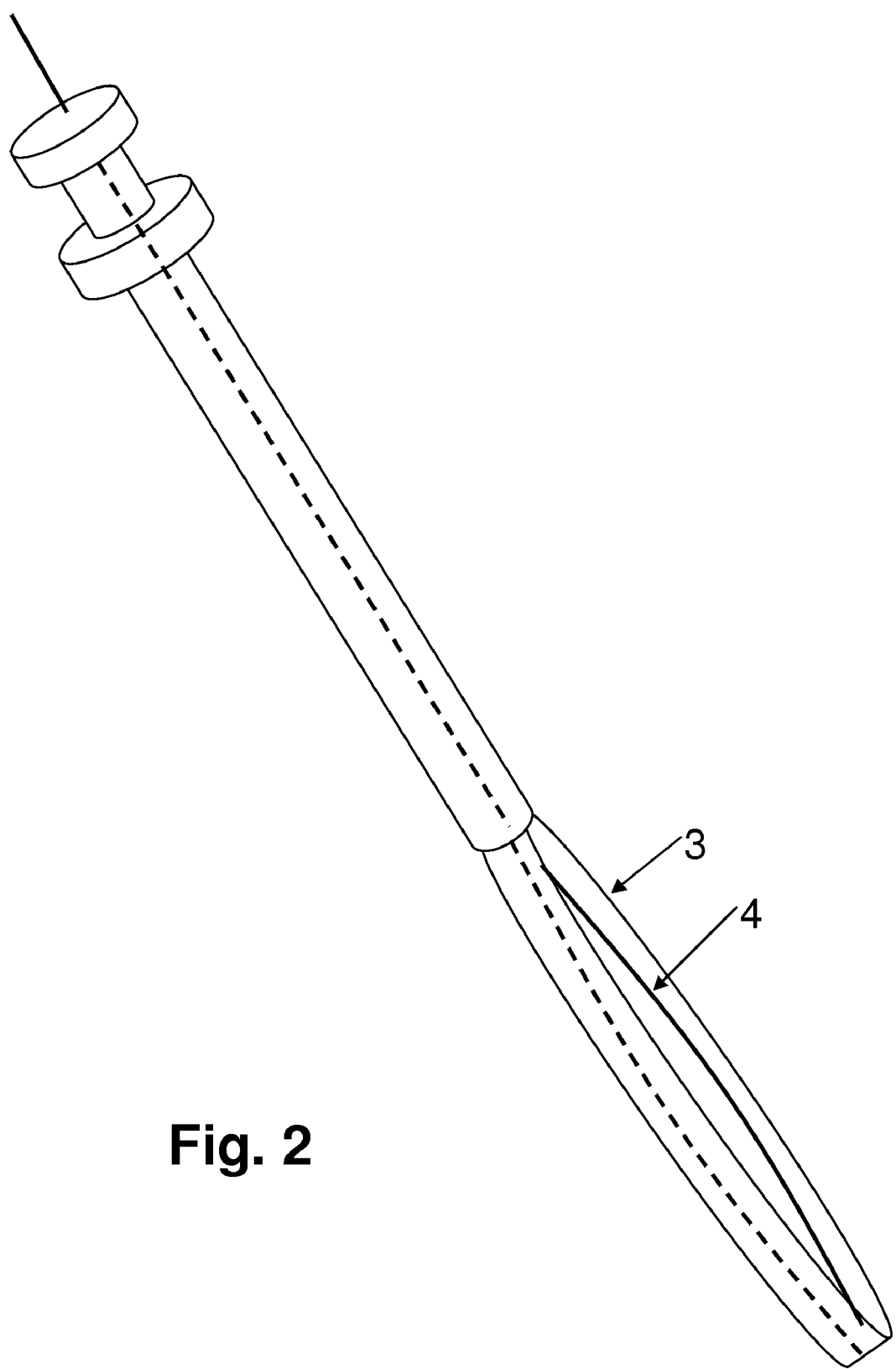
FIG. 2 provides another view of the instrument shown in FIG. 1 and shows an exemplary ribbon-like configuration of the outer ring.

FIG. 2 depicts the device in the open position with outer ring (3) and inner wire (4). The deployment of the two rings would typically be performed once the instrument is placed in the body in order to place the rings over the tissue to be excised.

Figure 3:
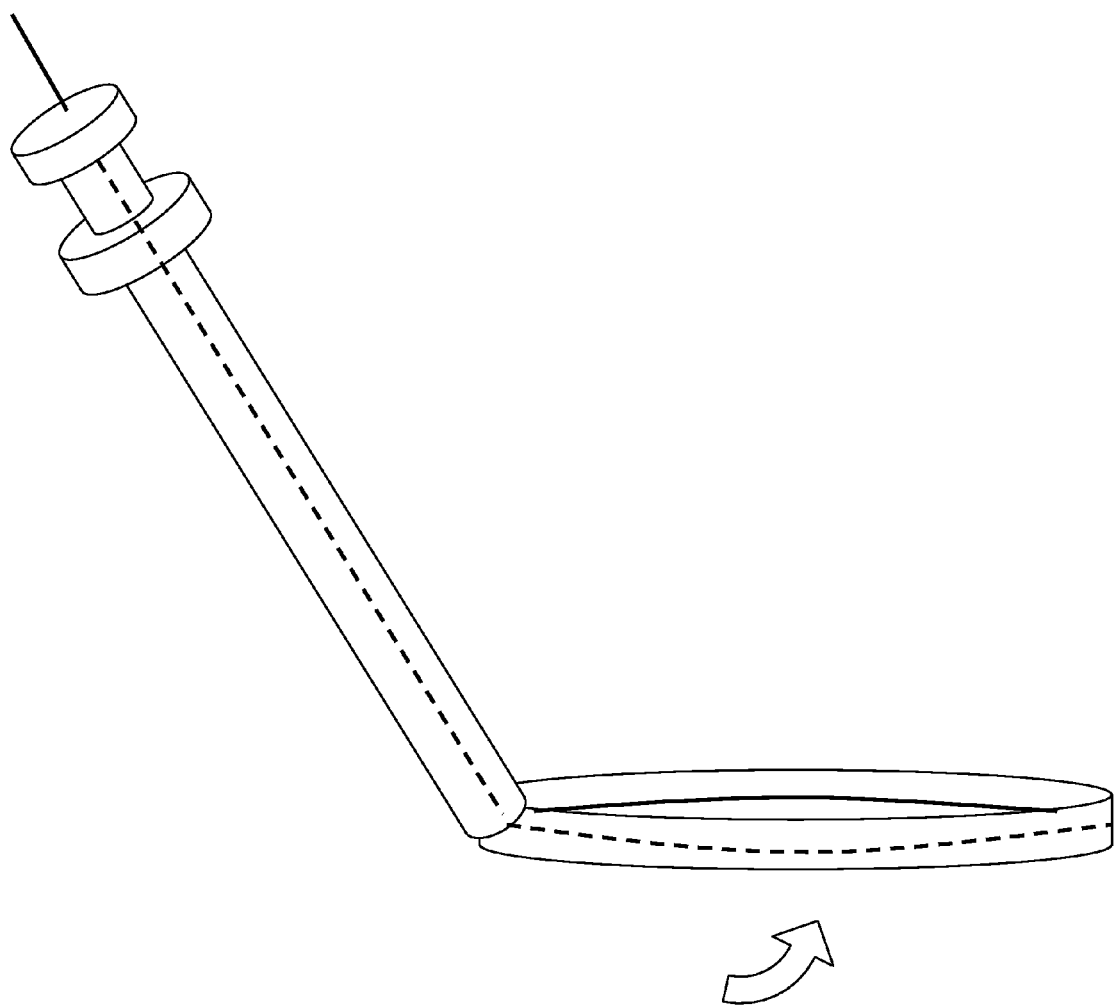
FIG. 3 depicts an embodiment in which the outer and inner rings are angled relative to the shaft.

FIG. 3 illustrates the ability of the outer and inner rings to bend after insertion in the abdomen. This might be required in order to position the rings over the uterine fundus and down to the level of the internal cervical os, which would be a typical placement for performing a supracervical hysterectomy.

Figure 4:
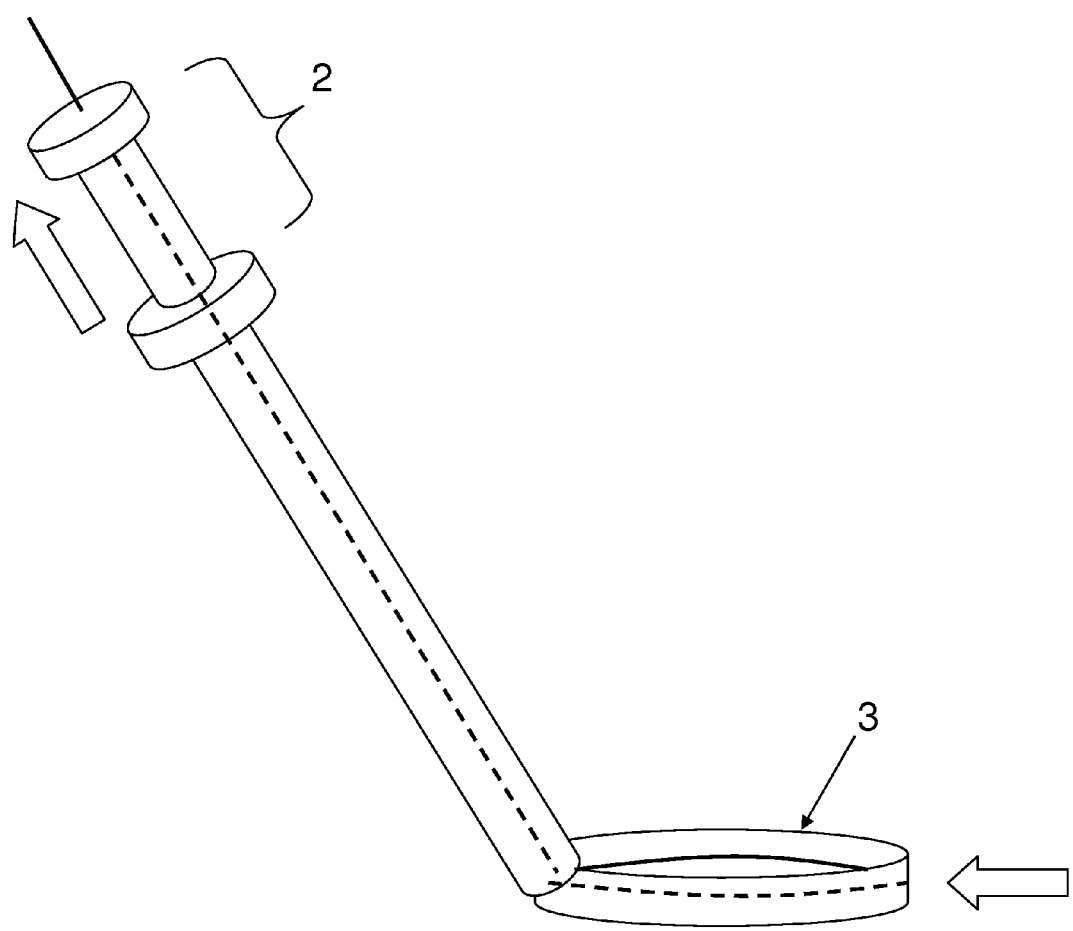
FIG. 4 illustrates movement of the handle to reduce the sizes of the outer and inner rings, in order to adjust the size of the rings around the tissues to be excised.

FIG. 4 demonstrates how the handle is pulled back in order to reduce the size of the outer and inner rings. The inner wire is attached to the handle so that both rings can be deployed and withdrawn together; however, the inner wire can be detached from the handle so that the inner wire can be drawn back independently of the outer wire for transection of tissues while maintaining the position of the outer stabilization ring on the cervix.

Figure 5:
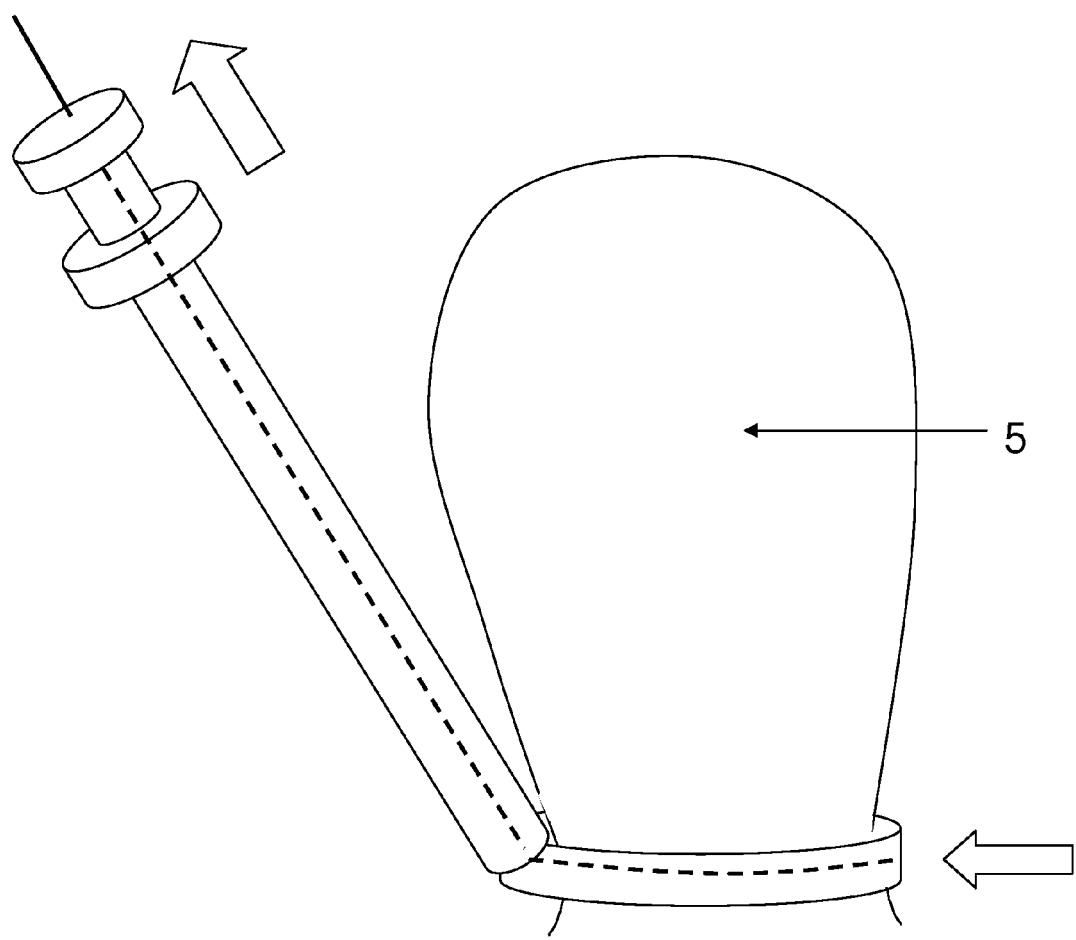
FIG. 5 demonstrates the positioning of the instrument over the uterine fundus and cinched down over the cervix.

FIG. 5 demonstrates the placement of the double rings at the level of the internal cervical os after the rings have been placed over the uterus (5).

Figure 6:
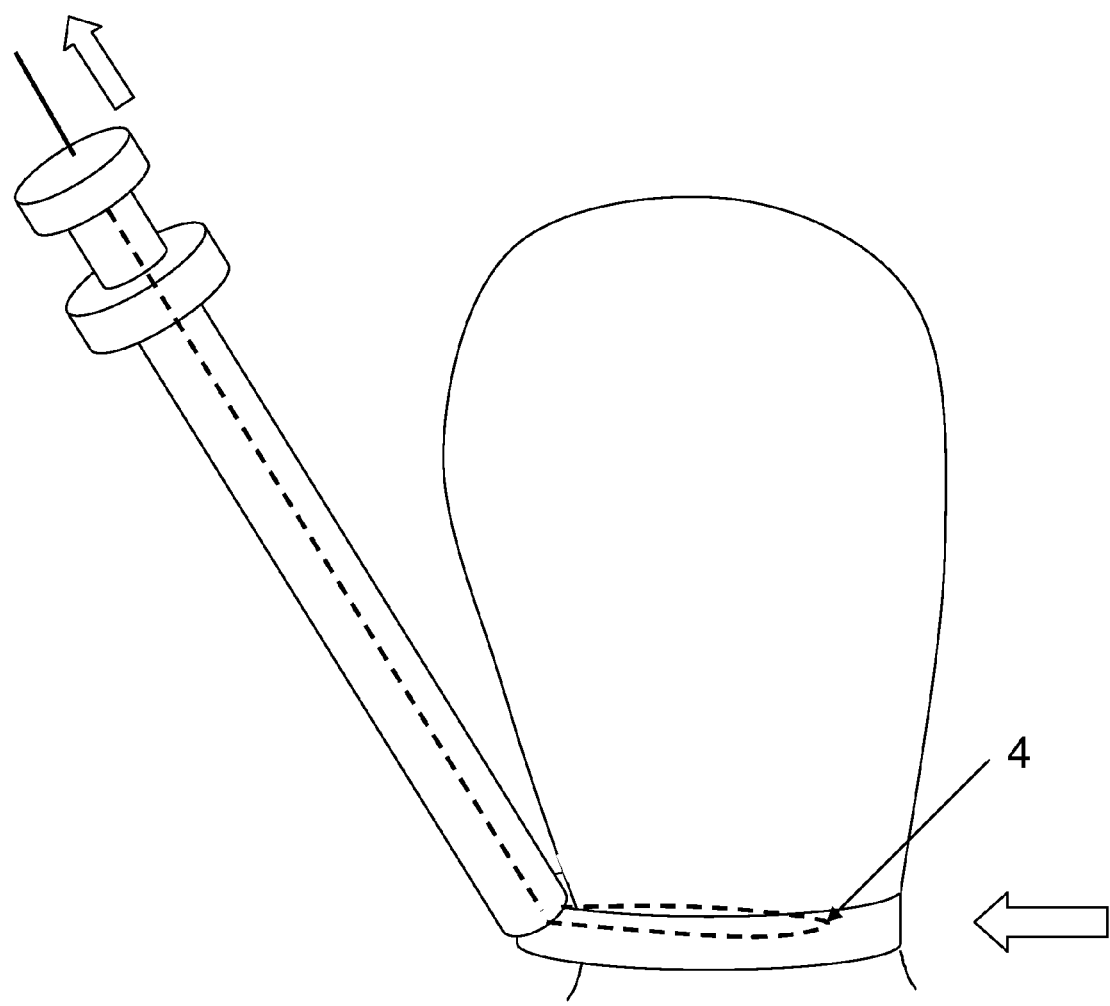
FIG. 6 illustrates the pulling of the inner transection wire through the cervix.

FIG. 6 illustrates the inner wire (4), having been separated from the handle, being pulled and withdrawn through the cervix while an electrical current is applied to the wire.

Figure 7:
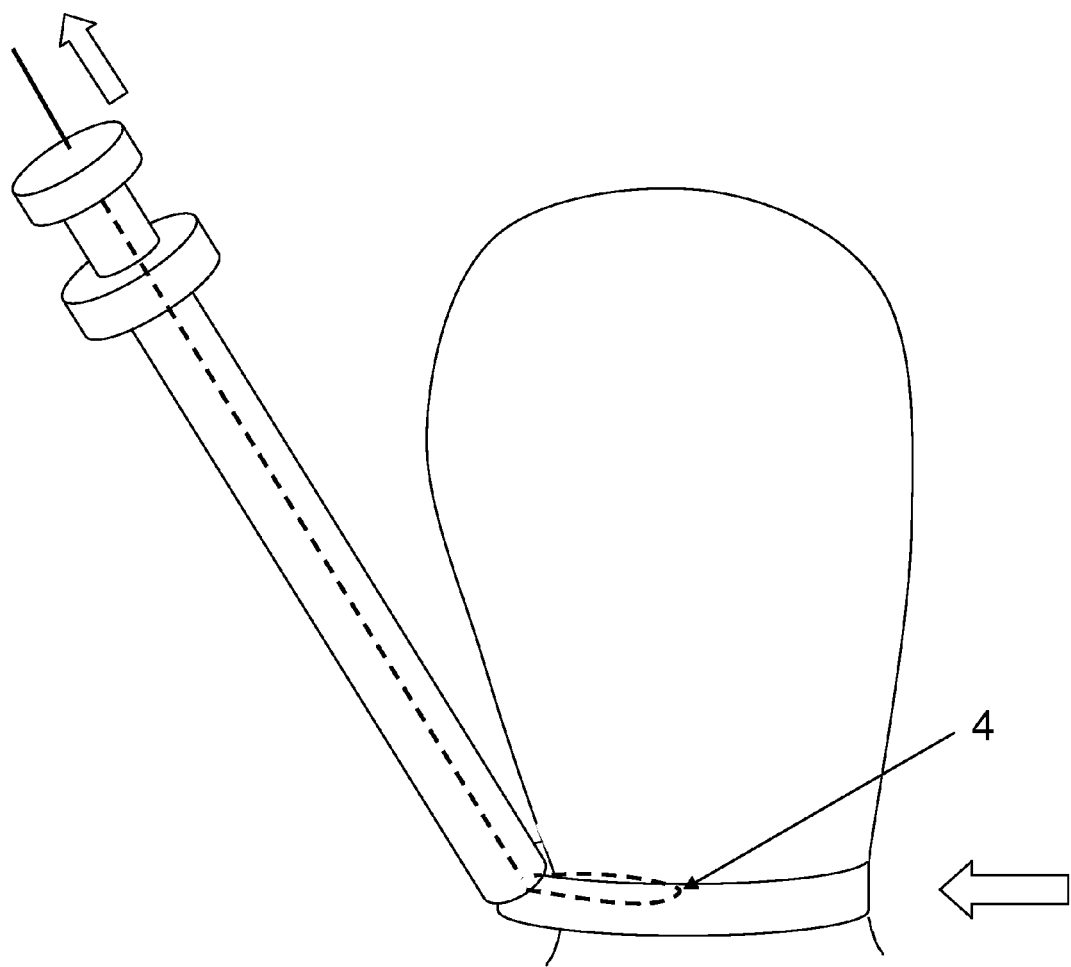
FIG. 7 illustrates the inner transection wire continuing to be pulled through the tissues and transecting through approximately half of the cervix.

FIG. 7 illustrates the inner wire (4) continuing to be pulled through the tissues with an electrical current applied. Before this step begins, the surgeon removes any uterine manipulator that has been placed into the cervix.

Figure 8:
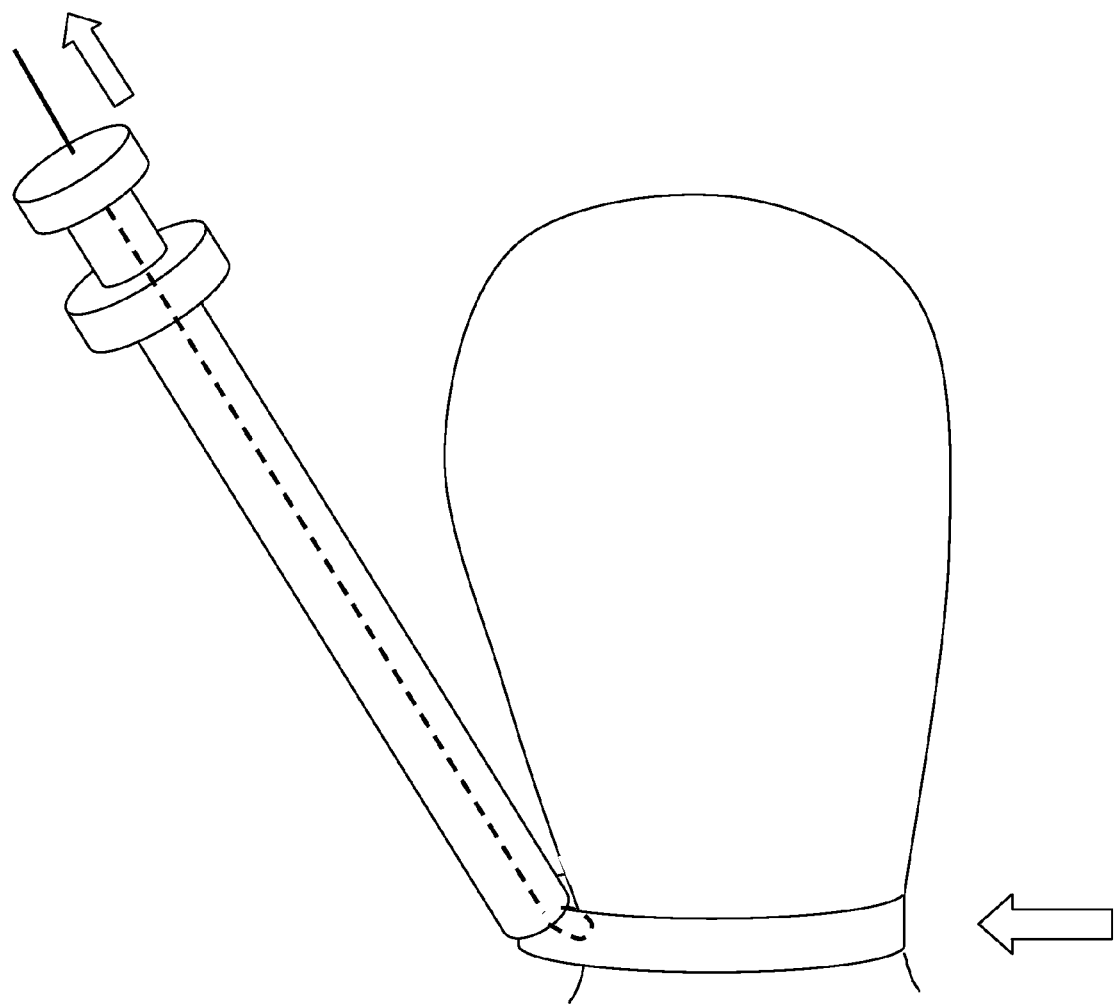
FIG. 8 demonstrates the inner transection wire almost completely pulled through the cervical tissue.

FIG. 8 illustrates the inner wire (4) has now been completely pulled through the tissue and has transected the uterine fundus.

Figure 9:
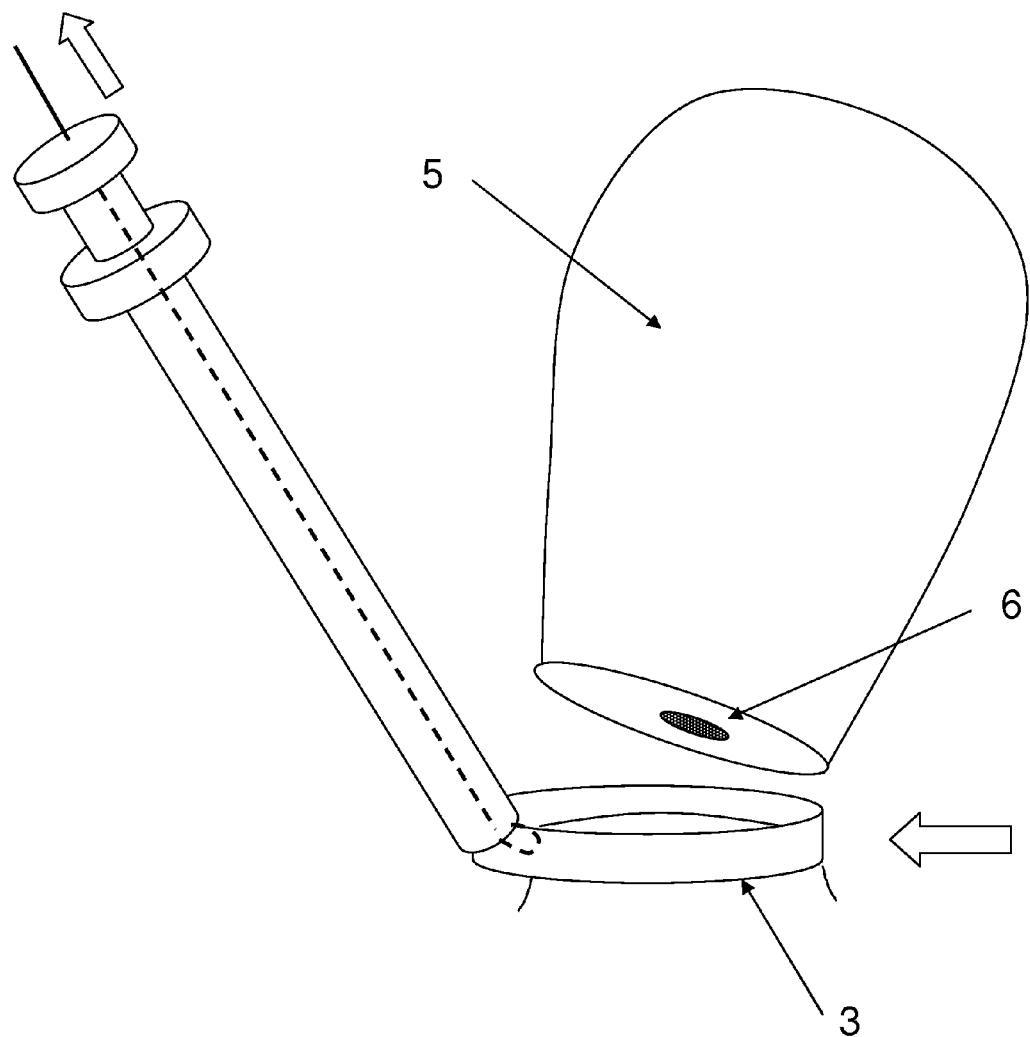
FIG. 9 demonstrates the completed transection through the cervix, after the inner transection wire has been withdrawn through the tissues and into the cylinder. The stabilization ring is still in place over the cervix.

FIG. 9 demonstrates the uterus (5) having been completely transected and the endocervical canal is now visible (6). The stabilization ring (3) is still around the cervix.

Figure 10:
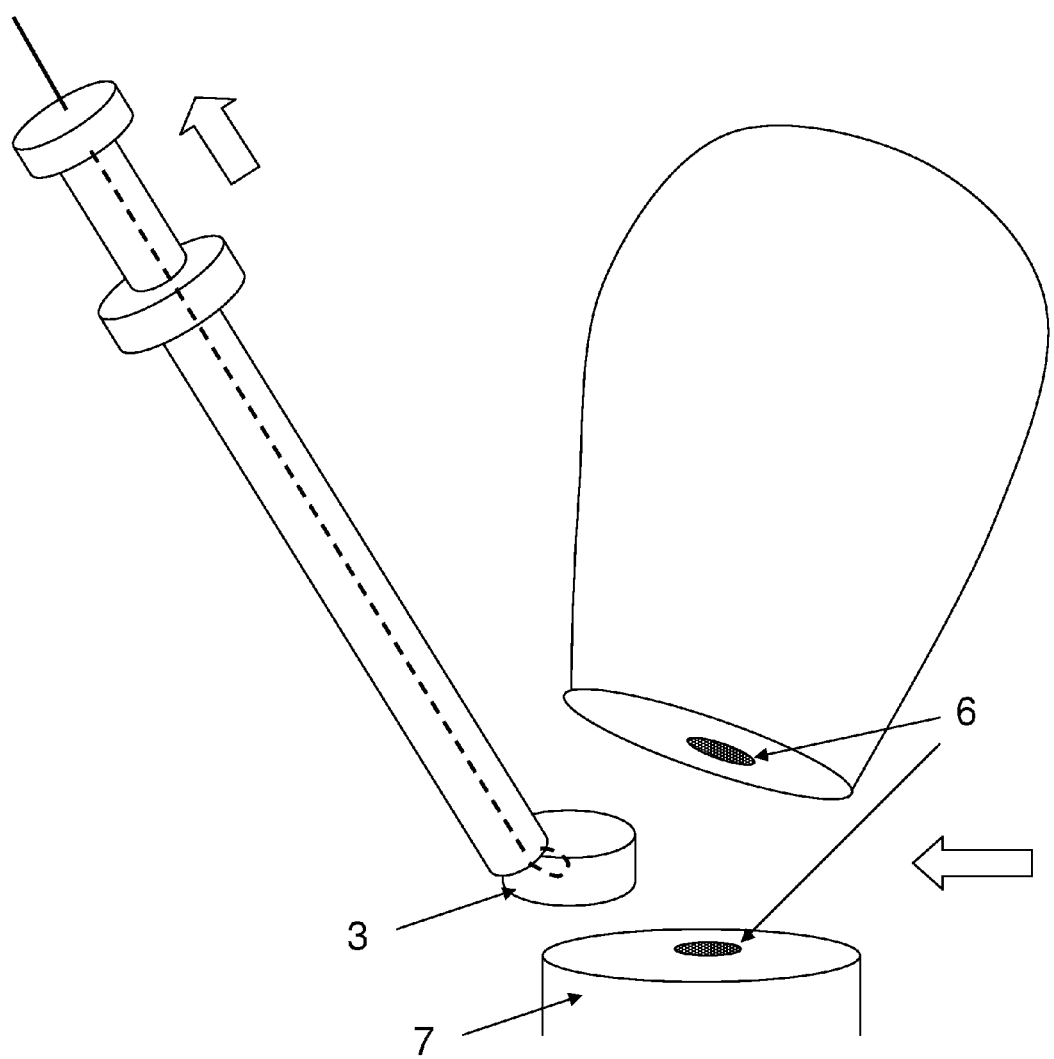
FIG. 10 demonstrates the cervix released from the stabilization ring and the stabilization ring being withdrawn back into the cylinder.

FIG. 10 demonstrates the endocervical canal (6) that can be visualized on the cervix (7) and on the uterine specimen. The outer stabilization ring (3) is being withdrawn back into the cylinder.

Figure 11:
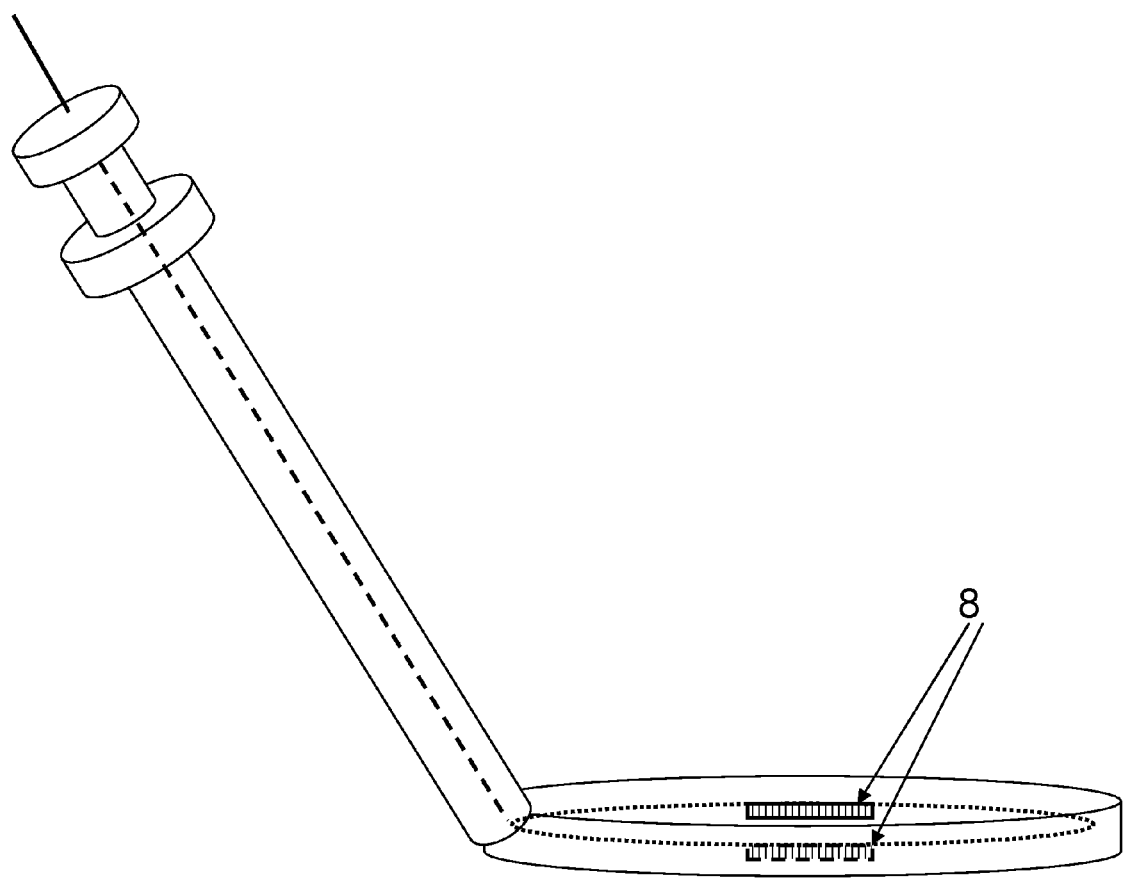
FIG. 11 demonstrates a second wire on the inner aspect of the outer ring that is exposed in only two separate areas, opposite from one another, in an area that would correspond to the location of the vascular supply to the uterus.

FIG. 11 demonstrates another embodiment of the instrument, where an exposed wire or other conductive material (8) is present on opposite sides of the outer ring, and is used to create a bipolar current with the inner wire (4) to coagulate vessels, such as the uterine vessels during the supracervical hysterectomy. In other embodiments, the wire (8) may be exposed at other or additional positions around the ring or may be exposed around the entire ring.

Figure 12:
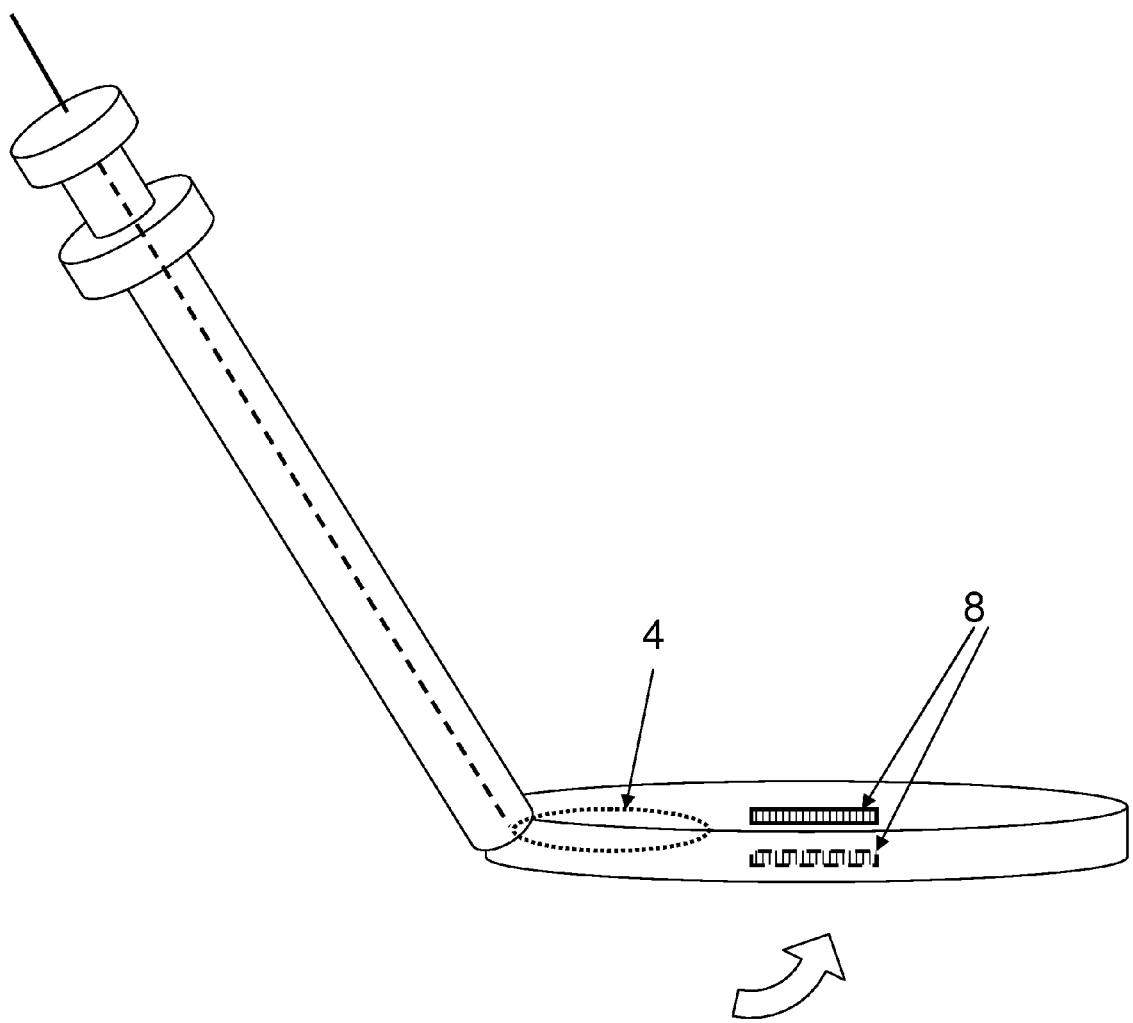
FIG. 12 illustrates the inner wire being withdrawn through the tissues and into the cylinder.

FIG. 12 demonstrates the inner wire (4) being pulled through tissue with monopolar cautery after bipolar cauterization of the vessels with both the inner wire (4) and the outer ring conductive elements (8).

Figure 13:
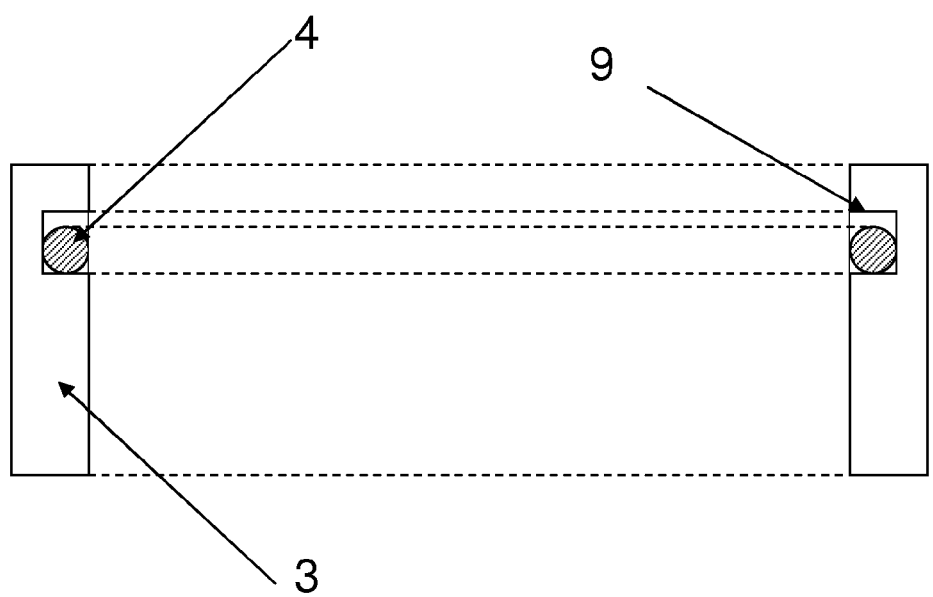
FIG. 13 illustrates a cross-section of an exemplary arrangement of the outer and inner rings.

FIG. 13 is a cross-section of one embodiment of the device with the inner ring (4) located within a groove (9) of the outer insulated ring (3).

Figure 14:
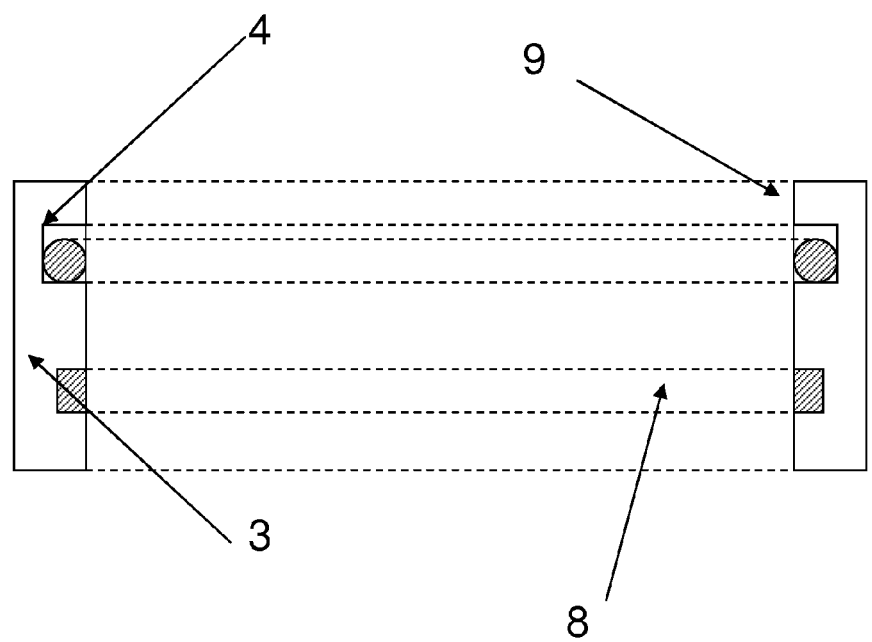
FIG. 14 shows a cross-section of another embodiment of the instrument, with a second wire that is within the outer ring, and is exposed circumferentially around the inner aspect of the outer ring.

FIG. 14 is a cross-section of another embodiment of the device with the inner ring (4), and the outer ring containing a conductive element (8) that is located circumferentially within or attached to the outer ring.

Figure 15:
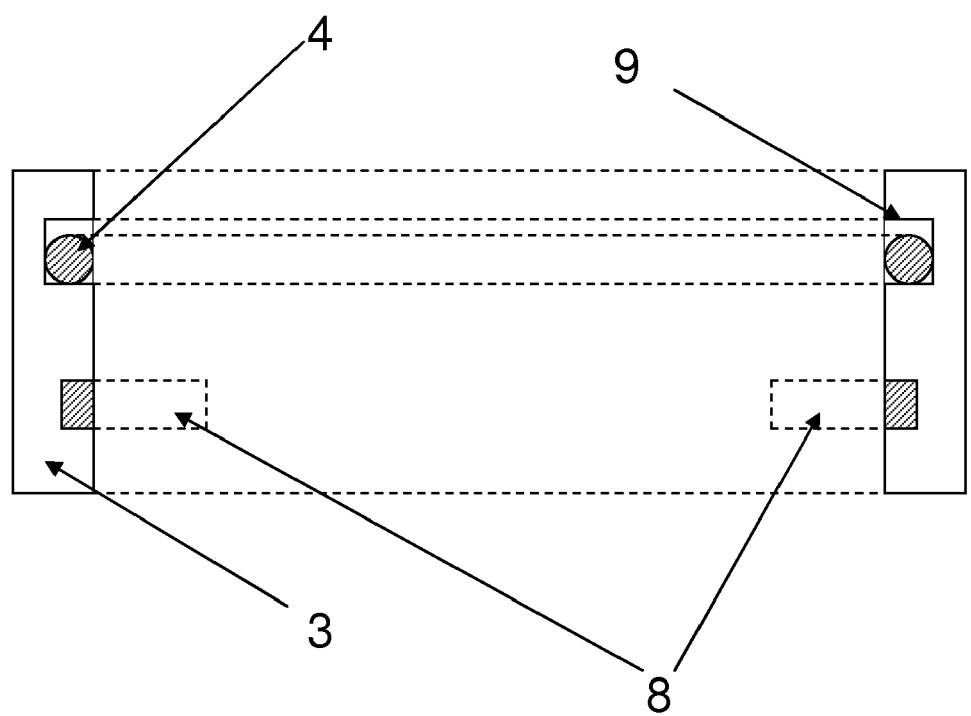
FIG. 15 shows a cross-section of another embodiment of the instrument, with a second wire that is within the outer ring, but is electrically exposed only on two opposite sides of the ring.

FIG. 15 is a cross-section of another embodiment of the device with the outer ring conductive elements (8) located at opposite ends of the outer ring.

Figure 16:
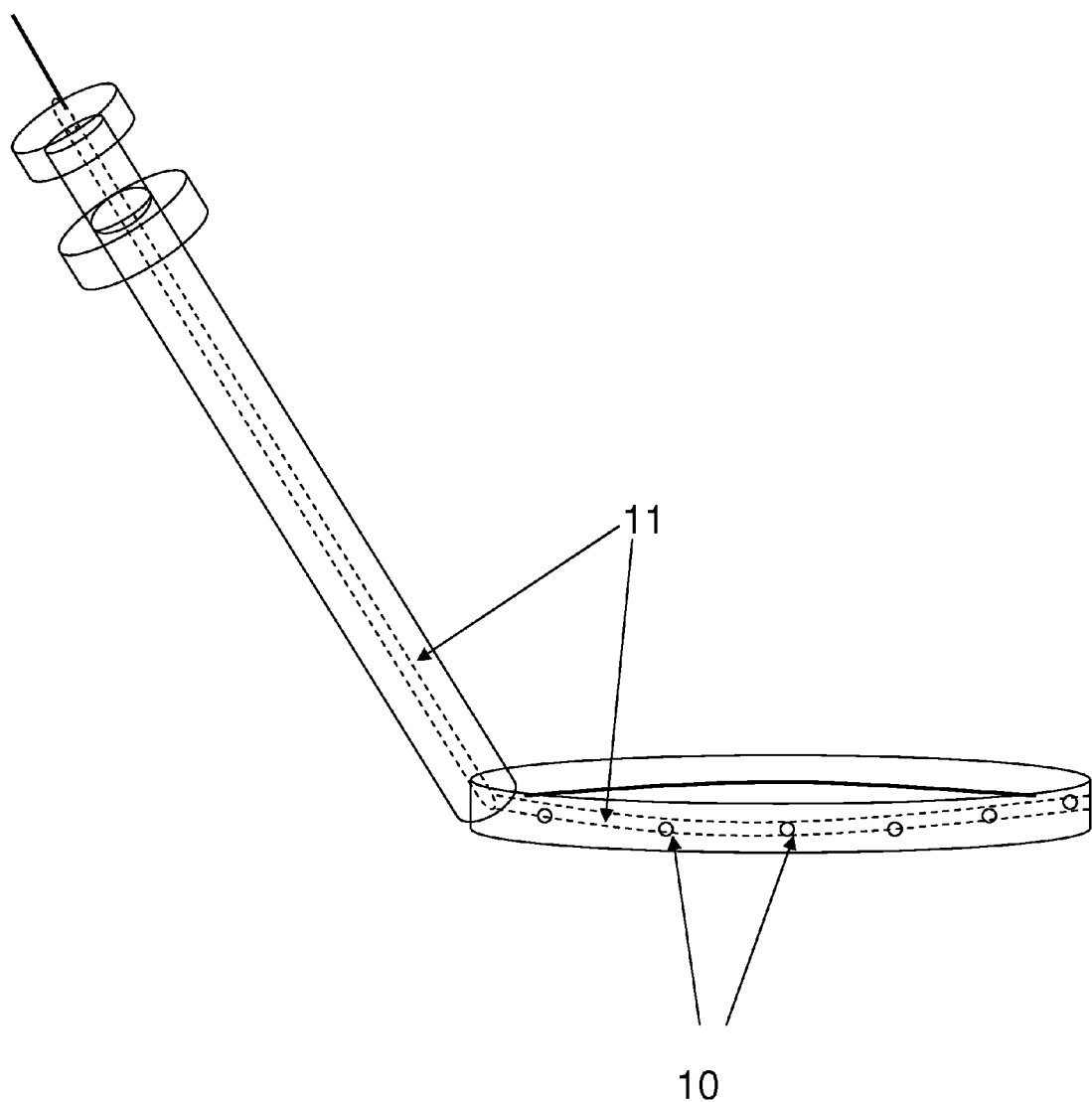
FIG. 16 illustrates the presence of smoke aspiration holes located around the circumference of the instrument, attached to a channel that travels up the shaft of the cylindrical instrument.

FIG. 16 demonstrates another embodiment of the outer ring, with a series of holes located on the outer ring (10) that are connected to a channel (11) that comes out from the handle of the instrument and is connected to suction (in order to evacuate smoke from the area during electrocoagulation of tissue, either with monopolar or bipolar energy) or to a fluid source for infusion of gas or liquid into the surgical site.

Figure 17:
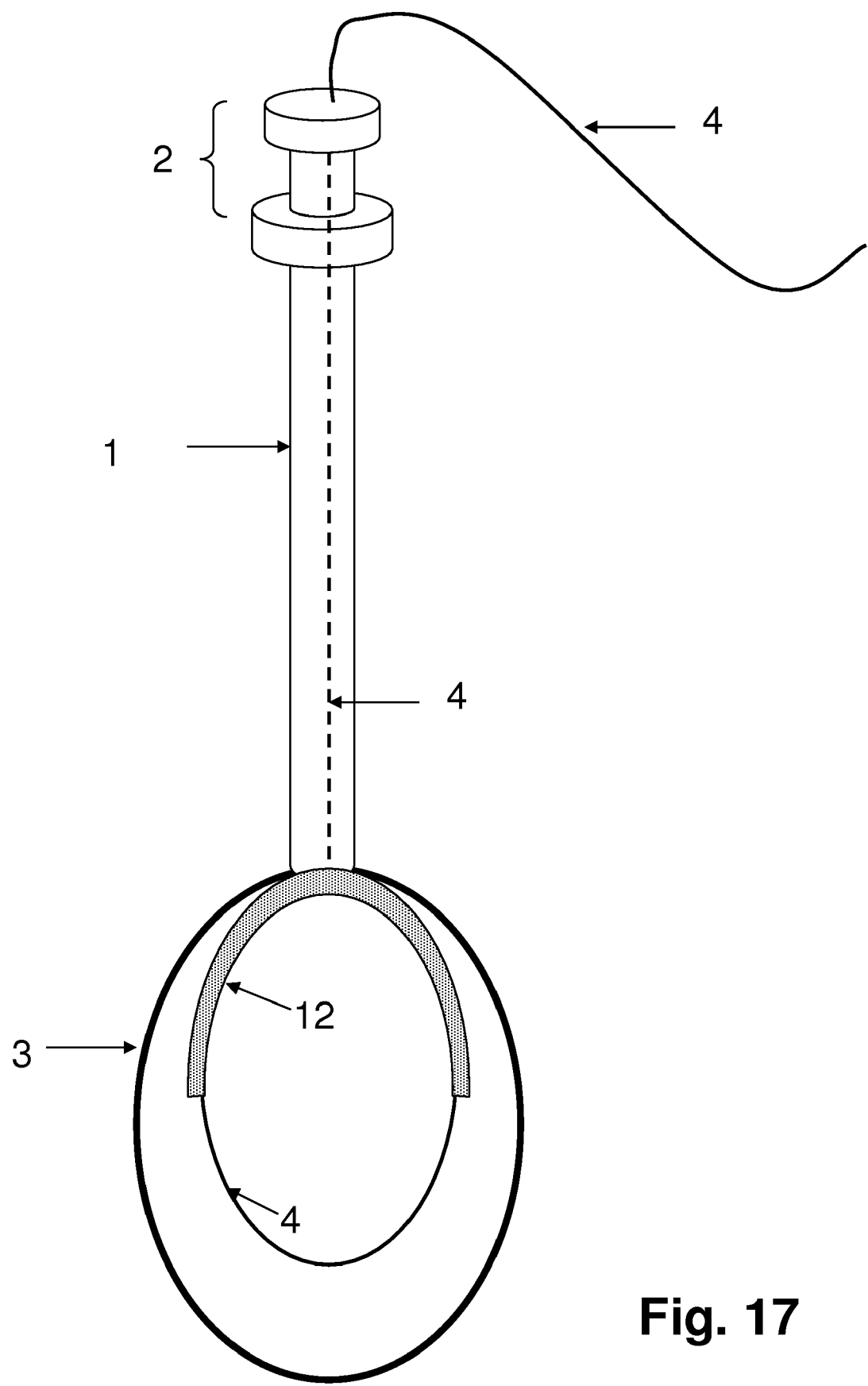
FIG. 17 illustrates another embodiment of the inner transection wire, which may be partially insulated proximally.

FIG. 17 illustrates another embodiment of the inner transection wire, whereby some part of the proximal wire is insulated (12).

Although the description and figures provided herein concern supracervical hysterectomy, the device itself can be used and/or is adaptable to be used with a wide variety of other anatomic portions, such as the gallbladder, liver, lung, pancreas, spleen, kidney, muscle, and bone. The device may also be used to remove pathological structures, such as polyps and neoplasms. Devices customized for particular anatomic regions or uses can be provided with predetermined sizes for the ring (3), wire (4), and/or element(s) (8), and optionally with predetermined number and position of element(s) (8).

We claim:

1. A laparoscopic cautery instrument comprising:
    an elongate shaft that:
        is sized and shaped for passage through a laparoscopic trocar port;
        defines at least one lumen along its length; and
        defines an aperture at a distal end of the shaft;
    a handle coupled to the shaft and moveable with respect to the shaft;
    an insulation ring that:
        has a ribbon shape;
        is formed at least in part by an electrical insulator;
        extends in a loop emanating from the shaft distal end; and
        is so operatively coupled to the handle as to be progressively expandable from and retractable into the shaft as the handle is moved with respect to the shaft, thereby increasing and decreasing the loop's size, respectively; and
    a monopolar cautery wire that:
        comprises an electrical conductor;
        has connector ends extending from a proximal end of the shaft and through the shaft lumen to form a wire loop emanating from the shaft distal end;
        is selectively operably coupled to the handle such that:
            when coupled to the handle:
                the wire loop is progressively expandable from and retractable into the shaft as the handle is moved with respect to the shaft, thereby increasing and decreasing the wire loop's size, respectively; and
                the wire loop contacts an inward-facing side of the ring loop during such progressive expansion and retraction; and
            when not coupled to the handle, at least one of the wire's ends is progressively retractable through the shaft, thereby decreasing the wire loop's size independently of movement of the ring loop.

2. The instrument of claim 1, further comprising an electrical power source to which the connector ends of the monopolar cautery wire are so coupled as to apply monopolar current to the monopolar cautery wire.

3. The instrument of claim 1, further comprising an electrical conductor affixed to the inward-facing side of the ring loop.

4. The instrument of claim 3, further comprising an electrical power source to which the wire connector ends and the electrical conductor are so coupled as to apply bipolar current between the wire loop and the electrical conductor.

5. The instrument of claim 4, wherein the electrical conductor comprises a pair of electrodes positioned at opposing locations of the ring loop.

6. The instrument of claim 4, wherein the electrical conductor comprises a conductor loop extending along at least half of the inward-facing side of the ring loop.

7. The instrument of claim 1, wherein a proximal portion of the wire is embedded in an electrical insulator.

8. The instrument of claim 1, a distal portion of the wire loop is free of electrical insulator.

9. The instrument of claim 1, wherein the insulation ring defines one or more apertures and a channel in fluid communication with the apertures.

10. The instrument of claim 9, further comprising a suction source in fluid communication with the channel.

11. The instrument of claim 1, further comprising a steering mechanism so coupled to the insulation ring as to permit deflection of the ring relative to the elongate shaft.

12. A laparoscopic cautery instrument comprising:
    an elongate shaft that:
        is sized and shaped for passage through a laparoscopic trocar port;
        defines at least one lumen along its length; and
        defines an aperture at a distal end of the shaft;
    a monopolar cautery wire that:
        comprises an electrical conductor; and
        has connector ends extending from a proximal end of the shaft and through the shaft lumen to form a wire loop emanating from the shaft distal end, and wherein at least one of the wire's ends is progressively retractable through the shaft, thereby decreasing the wire loop's size;
    an electrical conductor positioned at least in part proximate the monopolar cautery wire; and an electrical power source to which the wire connector ends and the electrical conductor are coupled, the electrical power source being operable in two modes such that:

in a first mode, the electrical power source delivers monopolar current through the monopolar cautery wire and no current through the electrical conductor; and in a second mode, the electrical power source delivers bipolar current between the monopolar cautery wire and the electrical conductor.

13. The instrument of claim 12, wherein the electrical conductor comprises a pair of electrodes positioned at opposing locations.

14. The instrument of claim 12, wherein the electrical conductor comprises a conductor loop.

15. The instrument of claim 14, further comprising an insulation ring that:

has a ribbon shape;
is formed at least in part by an electrical insulator;
extends in a loop emanating from the shaft distal end; and
is so operatively coupled to the handle as to be progressively expandable from and retractable into the shaft as the handle is moved with respect to the shaft, thereby increasing and decreasing the loop's size, respectively;
wherein the conductor loop extends along at least half of an inward-facing side of the ring loop.

16. A laparoscopic cautery method comprising:

advancing the instrument of claim 1 through a laparoscopic trocar so that the shaft distal end approaches a surgical site requiring cautery;
expanding the ring and wire;
fitting the ring and wire over an anatomical structure so that the ring loop and wire loop surround a portion of the anatomic structure;
applying monopolar current to the monopolar cautery wire; and
pulling at least one of the wire's ends, while the wire is not coupled to the handle, thereby:
retracting the wire;
pulling the wire through the surrounded anatomic structure; and
severing the anatomic structure by cautery.

17. The method of claim 16, wherein the instrument further comprises an electrical conductor affixed to the inward-facing side of the ring loop, and the method further comprises applying bipolar current between the wire and the electrical conductor.

18. The method of claim 16, wherein the insulation ring defines one or more apertures and a channel in fluid communication with the apertures, and the method further comprises suctioning fluid away from the surgical site.

19. The method of claim 16, wherein fitting comprises so snugly cinching the ring about the portion of the anatomic structure as to cause severed portions of the anatomic structure to be held by the ring following the severing.

20. A laparoscopic cautery method comprising:

advancing the instrument of claim 12 through a laparascopic trocar so that the shaft distal end approaches a surgical site requiring cautery;
expanding the wire;
fitting the wire over an anatomical structure so that the wire loop surrounds a portion of the anatomic structure;
applying bipolar current between the wire and the electrical conductor to cauterize another portion of the anatomic structure or another anatomic structure;
applying monopolar current to the monopolar cautery wire; and
retracting the wire, thereby:
pulling the wire through the surrounded anatomic structure; and
severing the anatomic structure by cautery.

* * * * *